(12) United States Patent
Ordóñez-Smith et al.

(10) Patent No.: US 8,897,861 B2
(45) Date of Patent: Nov. 25, 2014

(54) ELECTROCARDIOGRAPHIC METHOD AND APPARATUS BASED ON BIPOLAR, NON-VECTORIAL, TRUNCAL LEADS OR REAL UNIPOLAR LEADS

(75) Inventors: Jorge Hernando Ordóñez-Smith, Columbia, MD (US); Patricia Ordóñez, Laurel, MD (US)

(73) Assignee: Jorge Hernando Ordóñez-Smith, Columbia, MD (US)

( * ) Notice: Subject to any disclaimer, the term of this patent is extended or adjusted under 35 U.S.C. 154(b) by 136 days.

(21) Appl. No.: 13/541,697

(22) Filed: Jul. 4, 2012

(65) Prior Publication Data

US 2012/0316420 A1    Dec. 13, 2012

Related U.S. Application Data

(63) Continuation-in-part of application No. 11/163,140, filed on Oct. 6, 2005, now abandoned, and a continuation-in-part of application No. 12/554,979, filed on Sep. 7, 2009, now abandoned.

(51) Int. Cl.
   *A61B 5/0432*    (2006.01)
   *A61B 5/0402*    (2006.01)
(52) U.S. Cl.
   CPC ................................... *A61B 5/0402* (2013.01)
   USPC ......................................... 600/509; 600/523
(58) Field of Classification Search
   USPC ................................................. 600/508, 509
   See application file for complete search history.

(56) References Cited

U.S. PATENT DOCUMENTS

| | | |
|---|---|---|
| 1,882,402 A | 10/1932 | Kruse |
| 2,098,695 A | 11/1937 | Southwuck |
| 2,229,698 A | 1/1941 | Hollmann |
| 2,655,425 A | 10/1953 | Wood |
| 3,922,686 A | 11/1975 | France |
| 4,090,505 A | 5/1978 | Mortara |
| 4,121,575 A | 10/1978 | Mills |
| 4,184,487 A | 1/1980 | Peyer |
| 4,202,344 A | 5/1980 | Mills |

(Continued)

OTHER PUBLICATIONS

F. N. Wilson, C. E. Kossman, G.E.Burch, F. D. Johnston, E. Lepeschkin G. B. Myers, E. Goldberger, A. Graybiel, H. H. Hecht, Recommendations for Standardization of Electrocardiographic and Vectocardiographic Leads. Circulation 1954; 10: 564-573.

(Continued)

*Primary Examiner* — Allen Porter, Jr.

(57) ABSTRACT

The present invention consists of a modification and a new method of today's art 12 lead resting electrocardiogram The modifications include: Elimination of connecting means to record today's art Leads; connecting means to connect a common positive electrode, placed on the left leg, to all the positive terminals of the electrocardiographic amplifiers; connecting means to connect the negative electrodes, placed on the chest to the negative terminals of each individual electrocardiographic amplifier; reporting the results of the electrocardiogram including all the digital data sets obtained and calculated by the electrocardiograph in a disk, and a remote safe Data Bank for easy retrieval. A method of repograming the electrocardiograph calculator to calculate the second derivative of the maximal and minimal values of each structure of the myocardium at specific instants of the electrocardiographic trace calculate the value generated by the left leg and the values generated by each negative electrode.

3 Claims, 4 Drawing Sheets

(56) References Cited

U.S. PATENT DOCUMENTS

| | | | |
|---|---|---|---|
| 4,593,698 | A | 6/1986 | Athans |
| 5,307,818 | A | 5/1994 | Segalowitz |
| 6,721,593 | B2 * | 4/2004 | Anderson et al. ............ 600/523 |
| 7,647,094 | B2 | 1/2010 | Wei |
| 8,005,532 | B2 | 8/2011 | Wei |
| 2003/0013978 | A1 | 1/2003 | Schlegel et al. |
| 2006/0235318 | A1 | 10/2006 | Ordonez-Smith |
| 2008/0255464 | A1 | 10/2008 | Vincent |
| 2010/0010333 | A1 | 1/2010 | Ordonez-Smith |

OTHER PUBLICATIONS

C. E. Kossmann, D. A. Brody, G. E. Burch, H. H. Hecht, F. D. Johnston, C. Kay, E. Lepeschkin, H. V. Pipberger, G. Baule, A. S. Berson, S. A. Briller, D. B. Geselowitz, L. G. Horan and O. H. Schmitt.: Recommendations for Standardization of Leads and of Specifications for instruments in Electrocardiography and Vectorcardiography. Circulation 1967; 35: 583-602.

J. J. Bailey, A. S. Berson, A. Garson, Jr., L. G. Horan, P. W. MacFarlane, D. W. Mortara and C. Zywietz.:Recoonedations for standardization and specifications in automated electrocardiography: bandwidth and digital signal processing. A report for health professionals by an ad hoc writing group of the Committee on Electrocardiography and Cardiac Electrophysiology of the Council on Clinical Cardiology, American Heart Association. Circulation 1990; 81:730-739.

R. C. Schlant, R.J. Adolph, J.P. Dimarco, L.S. Dreifus, M.I. Dunn, C Fisch, A. Carson, Jr., L. J. Haywood, H.J.Levine and J.A. Murray.: Guidelines for electrocardiography. A report of the American College of Cardiology/American Heart Association Task Force on Assessment of Diagnostic and Therapeutic Cardiovascular Procedures (Cammittee on Electrocardiography) Circulation 1992; 85: 1221-1228.

H. Burchell, G. Fahr, H. Feil, H. E. B. Pardee, W. D. Stroud and C. J. Wiggers.: Minimum requirements for acceptable electrocardiographs. J.A.M.A. 1950; 143:654-655.

American Heart Association.: Supplementary Report by the Committee of the American Heart Association for the Standardization of Precordial Leads, Am. Heart J., 1938; 15: 235-239.

American Heart Association.: Standardization of Precordial Leads, Am. Heart J., 1938; 15: 107-108.

American Heart Association, American College of Cardiology and Heart Rhythm Society.: Recommendations for the Standardization and Interpretation of the Electrocardiogram. Part. I: The Electrocardiogram and its Technology. J. Am. Coll. Cardiol. 2007; 49: 1109-1127.

Einthoven, W., Fhar, G., de Waart, A.: On the Direction and Manifest Size of the Variations of Potential in the Human Heart and on the Influence of the Position of the Heart on the Form of the Electrocardiogram, Pflüger's Arch. F. Physiol., 1913; 150: 275-315. Translation of Hoff, H.E. and Sekelj P in Am. Heart J. 1950; 40 (2): 163-191.

Goldberger, E.: A Simple, Indifferent, Electrocardiographic Electrode of Zero Potential and a Technique of Obtaining Augmented, Unipolar, Extremity Leads, Am. Heart J., 1942; 23: 483-492.

Katz, L. N. and Korey, H.: the Manner in Which Electric Currents Generated by the Heart Are Conducted Away. Am. J. Physiol. 1935; 111: 83-90.

Mauro, A., Nahum, L. H., Sikand, R. S., and Chernoff, H.: Equipotential Distribution for the Various Instants of the Cardiac Cycle on the Body Surface of the Dog. Am. J. Physiol. 1952; 168: 584-591.

Mauro, A., Nahum, L. H., and Sikand, R.: Instantaneous Equipotential Distribution on the Thoracic Surface of Human Subjects With Cardiac Pathology. Journal Appl. Physiol. 1953; 5: 698-704.

Nahum, L. H.: A Critical Evaluation of Electrocardiography. Trans. Am. Coll. Cardiol. 1951; 1-2: 168-177.

Nahum, L. H.: A Critical Evaluation of Electrocardiography. Trans. Am. Coll. Cardiol. 1952; 2: 168-177.

Powsner, E. R., Nahum L. H., and Mauro A.: Body Surface Potential Distribution of an Intrathoracic Bipole as Related to Tissue Conductivity in Electrocardiography. Am. J. Physiol. 1954; 177: 467-476.

Ordonez-Smith, J. H.: Study on the theories of: "Einthoven's Equilateral Triangle", "Wilson's Central Terminal" and the "Unipolar Leads of Goldberg and Wilson", Rev. Col. Cardiol., 2000; 8: 139-150.

Ordonez-Smith, J. H.: Morfologia del Electrocardiograma: Una Nueva Teoria. Medicina, 2008; 30: 8-26.

Stilli M. S., et al.: Newer Data on the Configuration and Variability Ranges of Body Surface Maps in a Sample of Normal Subjects. J. Electrocardiol. 1988; 21(1); 1-14.

Taccardi, B.: Distribution of Heart Potentials on the Thoracic Surface of Normal Human Subjects. Circulation Res. 1963; 12: 341-352.

Taccardi, B.: Body Surface Mapping of Equipotential Lines during Atrial Depolarization and Ventricular Repolarization. Circulation Res. 1966; 19: 865-878.

Taccardi, B.: Body Surface Mapping and Cardiac Electric Sources. J. Electrocardiol. 1990; 23(Suppl.): 150-154.

Waller, A. D.: The Electromotive Properties of the Human Heart, Brit M. J., 1888; I: 751-754.

Wilson, F. N., Johnston, F. D., MacLeod, A. G., Barker, P. S.: Electrocardiograms That Represent the Potential Variations of a Single Electrode, Am. Heart J. 1934; 9: 447-458.

Wolferth, C. C., Levezey, M. M., Wood, F. C.: The Relationship of Lead I, Chest Leads from the C3, C4, C5 and C6 Positions, and Certain Leads Made from Each Shoulder Region: the Bearing of these Observations Upon the Einthoven Equilateral Triangle Hypothesis and Upon the Formation of Lead I. Am. Heart J. 1941; 21: 215-227.

Wolferth, C. C. and Livezey, M. M.: A Study of the Methods of Making So-Called Unipolar Electrograms. Am. Heart J. 1944; 27:764-782.

American Heart Association C. E. Kossmann, D. A. Brody, G. E. Burch, H. H. Hecht, F. D. Johnston, C. Kay, E. Lepeschkin, H. V. Pipberger, G. Baule, A. S. Berson, S. A. Briller, D. B. Geselowitz, L. G. Horan and O. H. Schmitt.: Recommendations for Standardization of Leads and of Specifications for instruments in Electrocardiography and Vectorcardiography. Circulation 1967; 35: 583-602.

Goldberger, E.: The Validity of the Einthoven Triangle Hypothesis, Am. Heart J. 1945; 29: 369-377.

* cited by examiner

ELECTROCARDIOGRAPHIC METHOD AND APPARATUS BASED ON BIPOLAR, NON-VECTORIAL, TRUNCAL LEADS OR REAL UNIPOLAR LEADS

CROSS-REFERENCE TO RELATED APPLICATIONS

This application is a continuation-in-part of patent application Ser. No. 11/163,140, filed Oct. 6, 2005 now abandoned; and a continuation-in-part of patent application Ser. No. 12/554,979, filed on Sep. 7, 2009 now abandoned by the present inventor, which are incorporated by reference.

REFERENCE TO A MICROFICHE APPENDIX

Not applicable

STATEMENT REGARDING FEDERALLY SPONSORED RESEARCH

Not applicable.

REFERENCES CITED

U.S. Patent Documents

| | | |
|---|---|---|
| U.S. Pat. No. 1,882,402 | Oct. 11, 1932 | R. H. Kruse |
| U.S. Pat. No. 2,098,695 | Nov. 09, 1937 | L. F. Southwick |
| U.S. Pat. No. 2,229,698 | Jan. 28, 1941 | H. E. Holmann |
| U.S. Pat. No. 2,655,425 | Oct. 13, 1950 | H. L. Wood |
| U.S. Pat. No. 2,678,867 | Mar. 18, 1954 | S. K. Rasmussen |
| U.S. Pat. No. 3,922,686 | Nov. 25, 1975 | L. R. France et al. |
| U.S. Pat. No. 4,090,505 | Mar. 23, 1978 | D. W. Mortara |
| U.S. Pat. No. 4,121,575 | Oct. 24, 1978 | H. Mills et al. |
| U.S. Pat. No. 4,184,487 | Feb. 21, 1980 | C. Peyer |
| U.S. Pat. No. 4,202,344 | May 13, 1980 | H. Mills et al. |
| U.S. Pat. No. 4,593,698 | Jun. 10, 1986 | R. J. Athans |
| U.S. Pat. No. 5,307,818 | Jun. 03, 1994 | Segalowitz |
| U.S. Pat. No. 7,647,094 | Jan. 12, 2010 | D. Wei |
| U.S. Pat. No. 8,005,532 | Aug. 23, 2011 | D. We |
| U.S. 2003/0013978 A1 | Jan. 16, 2003 | T. T. Schlegel et al. |
| U.S. 2008/0255464 A1 | Oct. 16, 2008 | G. M. Vin |

Other References

1. American Heart Association.: Standardization of Precordial Leads, *Am. Heart J.*, 1938; 15: 107-108
2. American Heart Association.: Supplementary Report by the Committee of the American Heart Association for the Standardization of Precordial Leads, *Am. Heart J.*, 1938; 15: 235-239
3. American Heart Association.: Recommendations for Standardization of Leads and of Specifications for Instruments in Electrocardiography and Vectorcardiography. *Circulation* 1967; 35 (3): 583-602
4. American Heart Association, American College of Cardiology and Heart Rhythm Society.: Recommendations for the Standardization and Interpretation of the Electrocardiogram. Part. I: The Electrocardiogram and its Technology. *J. Am. Coll. Cardiol.* 2007; 49: 1109-1127
5. Einthoven, W., Fhar, G., de Waart, A.: On the Direction and Manifest Size of the Variations of Potential in the Human Heart and on the Influence of the Position of the Heart on the Form of the Electrocardiogram, *Pflüger's Arch. F. Physiol.*, 1913; 150: 275-315. Translation of Hoff, H. E. and Sekelj P in *Am. Heart J.* 1950; (2): 163-191
6. Goldberger, E.: A Simple, Indifferent, Electrocardiographic Electrode of Zero Potential and a Technique of Obtaining Augmented, Unipolar, Extremity Leads, *Am. Heart J.*, 1942; 23: 483-492
7. Goldberger, E.: The Validity of the Einthoven Triangle Hypothesis. *Am. Heart J.*, 1945; 29: 369-377
8. Katz, L. N. and Korey, H.: The Manner in Which Electric Currents Generated by the Heart Are Conducted Away. *Am. J. Physiol.* 1935; 111: 83-90
9., Mauro, A., Nahum, L. H., Sikand, R. S., and Chernoff, H.: Equipotential Distribution for the Various Instants of the Cardiac Cycle on the Body Surface of the Dog. *Am. J. Physiol,* 1952; 168: 584-591
10. Mauro. A., Nahum, L. H., and Sikand, R.: Instantaneous Equipotential Distribution on the Thoracic Surface of Human Subjects With Cardiac Pathology. *Journal Appl. Physiol.* 1953; 5: 698-704
11. Nahum, L. H.: A Critical Evaluation of Electrocardiography. *Trans. Am. Coll. Cardiol.* 1951; 1-2: 168-177
12. Nahum, L. H.: A Critical Evaluation of Electrocardiography. *Trans. Am. Coll. Cardiol.* 1952; 2: 168-177
13. Ordóñez-Smith, J. H.: Study on the theories of: "Einthoven's Equilateral Triangle", "Wilson's Central Terminal" and the "Unipolar Leads of Goldberg and Wilson" *Rev. Col. Cardiol.*, 2000; 8: 139-150
14. Ordóñez-Smith, J. H.: Morfología del Electrocardiograma: Una Nueva Teoría. *Medicina,* 2008; 30: 8-26
15. Powsner, E. R., Nahum L. H., and Mauro A.: Body Surface Potential Distribution of an Intrathoracic Bipole as Related to Tissue Conductivity in Electrocardiography. *Am. J. Physiol.* 1954; 177: 467-476
16. Stilli M. S., et al.: Newer Data on the Configuration and Variability Ranges of Body Surface Maps in a Sample of Normal Subjects. *J. Electrocardiol.* 1988; 21(1): 1-14
17. Taccardi, B.: Distribution of Heart Potentials on the Thoracic Surface of Normal Human Subjects. *Circulation Res.* 1963; 12: 341-352
18. Taccardi, B.: Body Surface Mapping of Equipotential Lines during Atrial Depolarization and Ventricular Repolarization. *Circulation Res.* 1966; 19: 865-878
19. Taccardi, B.: Body Surface Mapping and Cardiac Electric Sources. *J. Electrocardiol.* 1990; 23(Suppl.): 150-154
20. Waller, A. D.: The Electromotive Properties of the Human Heart, *Brit M. J.,* 1888; I: 751-754.
21. Wilson, F. N., Johnston, F. D., Macleod, A. G., Barker, P. S: Electrocardiograms That Represent the Potential Variations of a Single Electrode, *Am. Heart J.* 1934; 9: 447-458
22. Wolferth, C. C., Levezey, M. M., Wood, F. C.: The Relationship of Lead I, Chest Leads from the $C_3$, $C_4$, $C_5$ and $C_6$ Positions, and Certain Leads Made from Each Shoulder Region: the Bearing of these Observations Upon the Einthoven Equilateral Triangle Hypothesis and Upon the Formation of Lead I. *Am. Heart J.* 1941; 21: 215-227
23. Wolferth, C. C. and Livezey, M. M.: A Study of the Methods of Making So-Called Unipolar Electrograms. *Am. Heart J.* 1944; 27:764-782

BACKGROUND OF THE INVENTION

1) Field of the Invention

The invention relates to modifying the electrocardiograph and a new method to record electrocardiograms by placing the electrodes on areas were the potentials of each of the heart structures are prevalent and pairing them with an electrode placed on the left leg. The use of the common electrode, in contrast to today's art of changing the polarity and using two, three, or four electrodes per lead, facilitates the recognition of the normal electrocardiogram, the abnormal pathological changes and the genesis of such anomalies.

2) Description of the Related Art

In 1,888, Augustus Desire Waller recorded the first electrocardiographic trace by immersing his assistant hands in containers with water connected to a mercury electrometer. Later the containers were filled with a saline solution. The two arms and the left leg were immersed in three separate containers and three leads were recorded connecting the leg to each arm and then the two arms together. The positive terminal of the mercury electrometer was connected to the leg and the arms to the negative terminal to record Lead II and Lead III and the left arm was connected to the positive terminal and the right arm to the negative terminal to record lead I. This arrangement is still done today (15. Waller, 1888; 751-754).

In 1,906, Wilhelm Einthoven invented the string galvanometer and the recordings became accurate and standardized. Since the detected electrocardiographic signals are in the range of 1 to 2 mV the recordings were obtained at a sensitivity of 10 mm/mV and a speed of 25 mm/sec. a standard still in effect today (1. AHA 1938, recommendation 5). By 1913 Einthoven, Fhar and de Waart demonstrated the mathematical relationship between the three leads III=II−I (4. Einthoven, 1913, in *Am. Heart J.* 1950, page 172 paragraph 48), known today as Einthoven's Law, and introduced the assumption of the Equilateral Triangle and the Central Dipole to calculate the electrical axis of the heart. With time Einthoven's assumption became known as today's Einthoven's Theory of the Equilateral Triangle and it's Rotating Central Dipole (4. Einthoven, 1913, in *Am. Heart J. pages* 175-176, FIG. 17, paragraphs 60-63; 3. AHA, 2007, page 1117, col. 1, lines 2-16).

Since the times of Waller to the mid-seventies the electrocardiographs had only one amplifier and a dial to select the lead to be recorded at the same sensitivity and speed established by Einthoven in 1913. The connecting cables of those electrocardiographs were color-coded: white to the right arm; black to the left arm; red to the left leg; green to the left leg (ground electrode). On 1,938 the Joint Recommendations of the American Heart Association and the Cardiac Society of Great Britain and Ireland, on page 108 the fifth recommendation establishes that any change in the sensitivity of one centimeter per millivolt should be recorded on the trace (1. AHA 1938, fourth paragraph of page 108). In the article Standardization of Precordial Leads, on page 235 third paragraph, establishes the placement of the chest leads, CF or V followed by a subscript number to designate the site of placement (2. AHA1938, third paragraph of page 235). The AHA in the article published in 1967 describes the requirements of the Direct-Writing Electrocardiographs (3. AHA 1967, page 585, col. 2, line 14), were the Gain of the electrocardiograph is reaffirmed (3. AHA 1967, page 586, col. 1, line 19-col. 2, line 12) The electrocardiographs then had a brown connecting means to be connected with the chest electrode placed on each of the specific sites of the chest. The selecting switch of the electrocardiograph connected the respective electrodes to record the desired lead. After the late sixties the CR, CL, and CF leads, that were considered bipolar leads, were eliminated.

In 1934, Frank N. Wilson et al. proposed that by joining three resistances of 5,000Ω in a junction, labeled Central electrode, and the other end of the resistances connected to the three extremities, based on Einthoven's theory and Kirchhoff's First Law, the electrical potential of the junction of the three resistors is equal to zero and so leads connected to the junction are unipolar. They introduced the nine unipolar leads known as $V_L$, $V_R$, $V_F$, $V_1$, $V_2$, $V_3$, $V_4$, $V_5$, and $V_6$ recorded by connecting the negative terminal of the amplifier to the central terminal and the positive terminal to the extremity to be investigated or to the chest electrodes (17. Wilson et al. 1934, equations 1-16). Today the three extremity leads, $V_L$, $V_R$, and $V_F$ are not recorded, (4. AHA, 2007, page 1115, col. 2, lines 33-36; col. 2, line 55-page 1116, line 3; page 1117, col. 2, lines 3-14 and lines 30-33).

In 1942, E Goldberger found that by eliminating Wilson's resistances and just connecting two extremities together to form a central electrode and connecting that junction to the third extremity the amplification of Wilson's extremity leads was increased by one half. He called these leads, the Augmented Unipolar Leads aVr, aVl and aVf. This was possible since, according to him, his three different central electrodes have a potential equal to zero too (6. Goldberger, 1942, equations on page 486). He preserved the polarity of Wilson's leads, negative terminal connected to the junction, positive terminal connected to the third extremity (6. Goldberger, 1942, page 485, FIG. 3). Today's electrocardiographs do not record Goldberger's leads; they are calculated from two recorded Einthoven leads (4. AHA, 2007, page 1117, lines 14-30).

All of today's electrocardiographs record at a sensitivity of 10 mm/mV. In special circumstances it can be halved, 5 mm/mV or doubled, 20 mm/mV. At the beginning of the tracing, the electrocardiographs show a square deflection showing the sensitivity. The sensitivity and the speed of the tracing is also printed at the bottom of the report. The standard speed been 25 mm/sec. can also be halved or duplicated in special cases. Einthoven set the sensitivity and speed of the electrocardigraphs in 1906 when he demonstrated his String Galvanometer at 10 mm/mV and a speed of 25 mm/sec. His electrocardiograph is still the standard that today's electrocardiographs have to meet to pass or fail, since none of them are as accurate and sensitive. It has no moving parts to print the electrocardiogram, and the response of the string in the magnetic field is free of any significant inertial forces.

Since the mid-seventies today's electrocardiographic art requires twelve leads: the three standard leads of Einthoven, Leads I, II and III, described by Einthoven in 1912, the three Augmented Unipolar Leads of Goldberger, aVr, aVl, and aVf, described by Goldberger in 1942, and the six Precordial Unipolar Leads of Wilson, $V_1$, $V_2$, $V_3$, $V_4$, $V_5$, and $V_6$, described by Wilson et al. in 1034 (4. AHA 2007, page 1115, col. 2, line 29-page 1116, line 3). All the leads use the R, L, F electrodes to record the standard extremity leads and the nine unipolar leads. Goldberger connects two extremities with a wire and the wire to the third extremity, Wilson connects the three extremities through 5,000Ω resistors to his central Terminal and the fourth electrode to one of the extremities, or to electrodes placed on the chest at the six sites established by the American Heart association in 1938 (2. AHA 1938; 15: 107-108; 3. AHA 2007, Page, 1117, col. 1, lines, 6-11; col. 2, lines, 1-33)

Today's electrocardiographs have eight amplifiers and record two of the Standard Leads of Einthoven and the six V Leads of Wilson simultaneously. The calculator of the electrocardiograph calculates the third Lead of Einthoven and the three aV Leads of Goldberger. The connecting means have ten cables that are marked: R, for the right arm, L, for the left arm, F, for the left leg, G or RL, for the right leg, and $V_1$ to $V_6$ for each of the chest leads sites. Since they have a computer on board they interpret or read the electrocardiograms, average the electrocardiographic signals, measure the width and height of the different waves and segments of the electrocardiographic signals. The sensitivity, 10 mm/mV, the speed of the recording, 25 mm/sec., and the polarity of the standard leads, I, II, III, remain unchanged since 1913. The polarity of the unipolar leads and the placement of the V electrodes have remained unchanged since the American Heart Association implemented them in 1938. The following U.S. patents corroborate the above statements. (U.S. Pat. No. 1,882,402, page 1 lines 24-35, page 2 line 120-page 3 line 5); (U.S. Pat. No. 2,098,695, col. 1, lines 36-40, col. 1, line 48-col 2 line 1); (U.S. Pat. No. 2,229,698 page 1 lines 9-15 and 30-38); (U.S. Pat. No. 2,655,425, col. 1, lines 1-7 and lines 24-44, col. 3, lines 19-28, line 73-col. 4, line 3 and col. 4, lines 13-23); (U.S. Pat. No. 3,922,686, col. 2, lines 14-17, col. 1, line 66-col. 2, line 1); (U.S. Pat. No. 4,090,505, col. 1, lines 28-56 and col. 2, lines 22-27); (U.S. Pat. No. 4,121,575, FIGS. 1: 5, 7, 9, 10, 11, and 12, col. 1 lines 24-51); (U.S. Pat. No. 4,184,487, col. 1, line 64-col, 2, line 1, col. 2, lines 3-9 and lines 30-33); (U.S. Pat. No. 4,202,344, col. 1, lines 45-53); (U.S. Pat. No. 8,005, 532. FIG. 1, FIG. 6); (U.S. 2003/0013978 A1, FIGS. 4, 5, and 6); (U.S. 2008/0255464 A1, FIG. 7)

An electrocardiographic trace is comprised of the following:

The P wave that represents the contraction of the auricle;

The PQR segment that represents an isoelectric state between the contraction of the auricles and the contraction of the ventricles;

The QRS complex that represents the depolarization of the ventricles and consists of the Q, R, and S waves. In a normal complex, one, two or all, waves can be present.

The ST segment that represents an isopotential state at the end of the QRS complex and the beginning of the T-wave;

The T-wave that represents the repolarization of the myocardium;

The U wave is seen occasionally and has no clear genesis, but a negative U-wave is strongly suggestive of myocardial infarction;

The TP segment represents what is considered the real isoelectric segment of the electrocardiographic trace. It is the time when both the ventricles and the auricles are relaxed.

3) Personal Research

Einthoven, after discovering his Law, LIII=LII−LI, assumed that if:

"the human body is represented as a flat homogeneous plate in the form of an equilateral triangle, RLF, s. FIG. 17." (5. Einthoven 1913, par. 61, page 292)

A small spot, H, in the middle of the triangle, represents the heart We can also represent the matters thus that between two closely adjacent points in the spot H a potential difference is developed. The arrow drawn in the figure coincides with the line that joins these points and represents the direction of the maximal potential difference in the heart" (5. Einthoven, 1913, par. 62-63, page 293).

Superimposing an equilateral triangle to an X-ray of the thorax demonstrates that the apex of the triangle only reaches the epigastrium, not the pubic synphysis, as is portrayed by Einthoven, Wilson and Goldberger. In rats and dogs do not reach even the myocardium. (14. Ordóñez-Smith 2008, page 11, FIG. 6).

The human body is not a

"flat, homogeneous plate in the form of an equilateral triangle"

rather, the electrical potentials that occur on the surface of the body in synchronicity with the contraction of the heart are conducted to the body surface in the manner demonstrated by Katz, et al. (8. Katz and Korey, page 83, lines, 12-18; page 85, Table 1; page 90, Summary) That is by the close contact of the different structures of surface of the heart with the spinal musculature, the musculature of the anterior and lateral walls of the chest, the abdomen, and the diaphragm.

The heart does not generate the changes of electrical potentials in or on the body as a dipole localized in "A small spot, H, in the middle of the triangle" (5. Einthoven, 1913).

In fact the auricles and the P wave are prevalent on:

In the right peri-clavicular areas;

The supra-sternal notch:

The lower left pre-sternal and precordial chest wall areas;

The epigastric area.

The changes of electrical potentials generated by the contraction of the right ventricle are prevalent on:

The anterior surface of the cephalic two thirds of the right hemi-thorax.

The electrical potentials generated by the contraction of the antero-lateral surface of the left ventricle are prevalent on:

The antero-lateral surface of the lower two thirds of the left hemi-thorax;

The left sub-axilar chest wall.

The electrical potentials generated by the contraction of the postero-inferior surface of the left ventricle are prevalent on:

The left sub-scapular and left inter-scapular areas of the left hemi-thorax;

The left lower back, and

The lower extremities. (14. Ordóñez-Smith, 2008; page 11)

The existence of Einthoven's dipole has not been demonstrated ever. On the contrary, Body Surface Mapping, done for many years, has demonstrated that the maximal or minimal potentials present on the anterior surface of the thorax at the time of the peak of the P, Q, R, S, T, and U waves are not represented at all on the posterior or lateral surfaces of the thorax (17. Taccardi, 1963, FIGS. 3d, 4a-c; 17. Taccardi, 1966, FIGS. 1c 1f and 3a-f: 16. Stilli, 1988, FIGS. 3 Pb-h, 6 QRSc-h and 6 ST-Td-h). A must if there was a dipole somewhere in Einthoven's plane, generating such changes. They have consistently demonstrated that the maximal and minimal potentials, at the instants of the peak values for the above-mentioned waves, are only present on the anterior area of the chest. A finding, that is impossible to happen if the potentials are generated by a dipole oriented in Einthoven's equilateral triangle plane as is accepted in today's electrocardiographic art. Studies with implanted dipoles have shown that the body is an homogeneous conductor of electrical potentials. (15. Powsner, E. R., FIGS. 2, 4-9, Summary, page 476).

Electrocardiograms with potentials similar to the potentials of the three standard leads of Einthoven, Leads I, II, and III, obtained by Wolferth, and Ordóñez-Smith placing the three standard electrodes on the surface of the left arm or just on the left shoulder would be impossible to obtain if the potentials were generated by a dipole placed somewhere within the heart. Those electrocardiograms demonstrate that the changes of potential present on the surface of the extremity are generated by other means (22. Wolferth et al 1941, FIG. 3, $C_1$-$C_3$, FIG. 4, $A_2$, $E_2$, FIG. 5, $A_2$, $B_2$, and $C_2$, Summary paragraphs 6-8 pages 226-227; 14. Ordóñez-Smith 2008, FIGS. 1-4).

The assumption devised by Einthoven to calculate the electrical axis of the heart, within the years, became the basis for Wilson's and Goldberger's theories of their Central Electrodes of zero potential. Einthoven's Law is valid because of simple mathematics, as Goldberger demonstrated in the appendix of his article, (6. Goldberger, 1945, page 377 under sub-paragraph Appendix), and Ordóñez-Smith has demonstrated the validity of the law as the result of a mathematical axiom not as a result of Einthoven's assumption (13. Ordóñez-Smith 2000, page 154, equations 1-4; 13. Ordóñez-Smith, 2008, pages 9-10 equations 1-8 and FIGS. 1-4).

Einthoven's Law refers to the addition of the potential differences between the three standard leads and not to the addition of the potentials of the three extremities as Wilson assumes. In order to obtain a zero potential by adding the potential differences between the three extremities at the peak of the R-wave, one or two of the values would have to be negative and equal to one or the addition of the positive values, a fact that is against the First Law of Kirchhoff, also known as the Law of the junctions:

$$I_1 + I_2 \ldots + I_{n-1} + I_n = 0 \qquad (1)$$

That Law states that the addition of the currents into a junction is equal to the addition of the currents out the junction. The electrons flow from the negative pole to the positive poles. The electrons into the junction have a positive sign and the electrons out the junction have a negative sign. To measure a drop of potential, the positive terminal of the voltmeter is placed on the highest positive potential and the negative terminal on the lowest potential. Within the circuit formed by Wilson's three resistors the current will flow from the extremity with the highest negative potential to the extremities with the lowest negative potentials or the highest positive potentials.

At the peak of the R wave the right arm has the highest negative potential (17. Taccardi, 1963. FIG. 4b), and the current flows into the junction (central terminal), a series circuit. All the electrons that flow through the resistor, connected to the right arm, go into the junction. From the junction (central terminal) the electrons leave the junction through the resistors connected to the two left extremities, a parallel circuit, with a higher positive potential. A 5,000Ω resistor in a series circuit keeps its value; two 5,000Ω resistors in a parallel circuit have the conductivity of a lesser resistance. Since the two extremities do not have the same potential, the extremity with the highest positive potential will have the greater flow and the other a lower flow. The rule of voltages in a parallel circuit state that the drop of potential of the parallel circuit is equal to each of the drops of potential within the circuit:

$$V_t = V_1 = V_2 = \ldots = V_{(n-1)} = V_n \qquad (2)$$

The current flowing into a junction that leaves the junction through a parallel circuit of two equal positive voltages and resistances will leave the junction with half of the current going through each resistance:

$$I_1 = I_1/2 + I_1/2 \qquad (i)$$

According to equation (2) the drop of potential of the entire parallel circuit is equal across all the resistors in the circuit. The drops of potential across the series circuit and across the parallel circuit are not equal:

$$5,000 I_1 \neq 5,000 I_1/2 \qquad (ii)$$

$$V_1 \neq V_1/2 \qquad (iii)$$

The voltages in equation (iii) are both positive. A fact, that goes with the Second Law of Kirchhoff.

$$V_t = V_1 + V_1/2 \qquad (iv)$$

Within the circuit formed by the three resistors of Wilson, $V_t$ is equal to the addition of the drop of potential across the series and parallel circuit, $$V_t = V_{series} + V_{parallel} \qquad (v)$$

Equation (iv) and (v) demonstrate that there is no place for the assumption that a dipole can generate the changes of potential associated with the heartbeat on the surface of the body. All the drops of potential across the three resistors of Wilson have to be positive. The electrical potential of Wilson's Central Terminal is equal to the total drop of potential of the circuit, minus the drop of potential of the parallel circuit (14. Ordóñez-Smith, 2008, FIG. 11, right lower diagram), o equal to $V_1$ in equation (iv) or to $V_{series}$ in equation (v). A value between, lower than $V_t/2$ and $2V_t/3$ depending on the potentials in the left extremities. Far from zero or near zero as assumed by Wilson. The potentials of the left extremities are, according to the Body Surface Maps, less negative or more positive than the right arm (17. Taccardi, 1963. FIG. 4b).

Equation (4) of Wilson has mathematical and physics errors:

$$(V_A - V_T) + (V_B - V_T) + (V_C - V_T) = r(I_A + I_B + C) \qquad (4)$$

(21. Wilson et al. 1934 page 449, last line)

The left side of the equation was calculated assuming that all the currents go into the junction (21. Wilson et al. 1934 page 449, last sentence of first paragraph after subtitle Potential of the central Terminal), an assumption that goes against Kirchhoff's First Law that states that any current that goes into a junction has to leave the junction. The left arm of the equation, written according to Wilson's FIG. 1, demonstrates that Wilson really believed that all the currents went into the Central Terminal no current went out of the junction:

$$(V_R - V_T) + (V_L - V_T) + (V_F - V_T) \qquad (vi)$$

According to Kirchhoff's First Law, the current passing through the resistance connected to the right arm is equal to the addition of the currents leaving the junction. Since the potential of the right arm is lower than the potential of the central terminal:

$$-(V_R - V_T) = (V_L - V_T) + (V_F - V_T) \qquad (vii)$$

Expressing the voltage in function of resistance multiplied by intensity (Ohm's Law):

$$-R_R I_R = R_L I_L + R_F I_F \qquad (viii)$$

Eliminating the value of the resistance we have:

$$-I_R = I_L + I_F \qquad (ix)$$

The algebraic addition of the currents going through the junction, following the rationality of equation (4) of Wilson, will be:

$$-I_R + -(I_L + I_F) \neq 0 \qquad (x)$$

Since $V_T$ is connected to the negative terminal and $V_T$ is positive with respect to $V_R$, the value of $(V_R - V_T)$ is negative, but the currents out the junction to the left extremities, $V_L$ and $V_F$, are positive with respect to $V_T$ and are recorded as positive. It can be said, without any error, that Wilson's assumption expressed in equation (4) does not follow Kirchhoff's First Law.

The right hand side of the equation does not take into account the fact that resistors in series keep their value, but resistors in parallel do not. In a series circuit the total resistance is:

$$R_t = R_1 + R_2 + \ldots R_{(n-1)} + R_n \quad (3)$$

In a parallel circuit the resistance is equal to:

$$R_t = 1/R_1 + 1/R_2 + \ldots + 1/R_{(n-1)} + 1/R_n \quad (4)$$

A mathematically and physics correct right arm equation is:

$$5{,}000 I_R + < 5{,}000(I_L + I_F) \quad (xi)$$

Since according to Kirchhoff's first Law, $I_R$ is equal to $(I_L + I_F)$ the right arm of the equation is not equal to zero either. The resistances are not equal, the resistance in the series circuit has a value of 5,000Ω but the two resistors of 5,000Ω in the series have a value inferior to the 5,000Ω. It could be between 2500Ω and less of 5,000Ω. As a consequence, it can be said, without any error, that all formulas derived from Wilson's equation (4) are wrong.

As can be appreciated from the foregoing discussion there is a very strong evidence demonstrating that today's accepted electrocardiographic theories are not valid. There is a need of having a better way to record and analyze the electrical potentials generated in association with the contraction of the heart. Some of the researchers with a similar view are: (23. Wolferth, et al. 1944, Summary 2. pages 780-781; 10. Nahum, 1951 FIGS. 3 and 4, Summary, page 177; 15. Stilli et al., 1988, FIGS. 3-8; 19. Taccardi 1990, pages 150-151, second to fourth paragraphs; 18. 1966, FIGS. 1-3; 16. 1963, FIGS. 3-5; 9; 9. Mauro A. et al., 1952, FIGS. 1 and 2, page 590, Summary, 9. 1953, FIGS. 1-4, page 794, Summary; 15. Powsner, E. R., FIGS. 2, 4-9, page 476, Summary,).

Since today's so called unipolar leads are bipolar, the new method consists of obtaining from 15 to a 100 Bipolar, Non-Vectorial, Truncal Electrocardiographic Leads, by standardizing the leads to a common positive electrode placed on the left leg and placing the negative exploring electrodes on: the right peri-clavicular area, supra-sternal notch, the anterior surface of the chest, epigastric area, left lateral chest wall, right and left axilar areas, right upper posterior axilar area and on the left posterior para-spinal area where the potentials generated by the heart are more prevalent and calculating twelve to thirty second derivatives pairing and subtracting the minimal from the maximal values recorded by the leads at the mid-ascending, peak and mid-descending values of the different waves, P, Q, R, S, T and U and at the PQR segment, RST segment, TU segment and TP segment. The use of exploring negative and common positive electrodes would facilitate the interpretation and analysis of the changes generated by the contraction of the heart.

OBJECTIVES AND FEATURES OF THE INVENTION

It is an objective of the present invention to obtain data that are more reliable and characteristic of the potential differences generated by the contraction of the different structures of the myocardium in its normal and abnormal states.

It is an objective of the present invention to modify the electrocardiograph to obtain Bipolar, Non-Vectorial, Truncal Leads by eliminating the connecting means to record the three Einthoven Standard Extremity Leads, L-I, L-II, and L-III, the three Goldberger Unipolar Extremity Leads, aVr, aVl, and aVf, and the six Wilson's Unipolar Precordial Leads, $V_1$, to $V_6$.

It is a further objective of the present invention to modify the electrocardiograph's calculator to obtain a second derivative of the recorded Bipolar, Non-Vectorial, Truncal Leads by pairing the maximal and minimal values generated by the heart on the torso at 30 specific instants of the electrocardiographic trace.

It is a further objective of the present invention to modify the electrocardiograph's analyzer to generate the approximate values generated by each electrode.

It is a further objective of the present invention to provide a method of enhancing and facilitating the recognition of the differences on the changes of potential on the body surface that are pathognomonic in the presence of myocardial pathology.

It is a further objective of the present invention to provide a method of analysis of the different changes of potential on the surface of the body to facilitate the recognition of normal and abnormal electrocardiographic patterns.

It is a feature of the present invention to acquire the changes of potential on the surface of the body that occur in synchronization with the contraction of the heart at sites that are closer to the heart and in the areas where the potentials generated by each different structure of the myocardium are prevalent.

It is a further feature of the present invention to analyze the changes of potential on the surface of the body that occur in synchronization with the contraction of the heart as a result of characteristic conduction patterns of the monophasic electrical potentials toward the body surface.

It is a further feature of the present invention to calculate the second derivatives of the Bipolar, Non-Vectorial, Truncal Leads to calculate the values generated by each Exploring Negative Electrode and the approximate values generated by the Common Positive Electrode.

It is a further feature of the present invention to calculate the second derivative between the maximal and minimal values at 30 instants of the electrocardiographic trace.

It is a further feature of the present invention to preserve, on a "Digital Disk", all the identified electrocardiographic digital data sets, including the subject's identification, the exact anatomical placement of the electrodes used for the electrocardiographic recording, and a short medical history.

It is a further feature of the present invention to compare the stored identified electrocardiographic digital data sets with the newly obtained identified electrocardiographic digital data sets by the electrocardiograph and to report, by the electrocardiograph, any differences between the two tracings.

It is a further feature of the present invention to report and save any differences between the Previous and new identified electrocardiographic digital data sets for further evaluations.

BRIEF DESCRIPTION OF THE DRAWINGS

This invention and its advances over the prior art can best be understood by reading the specification which follows in conjunction with the drawings herein, in which; according to one embodiment of the present invention.

Figure 1:
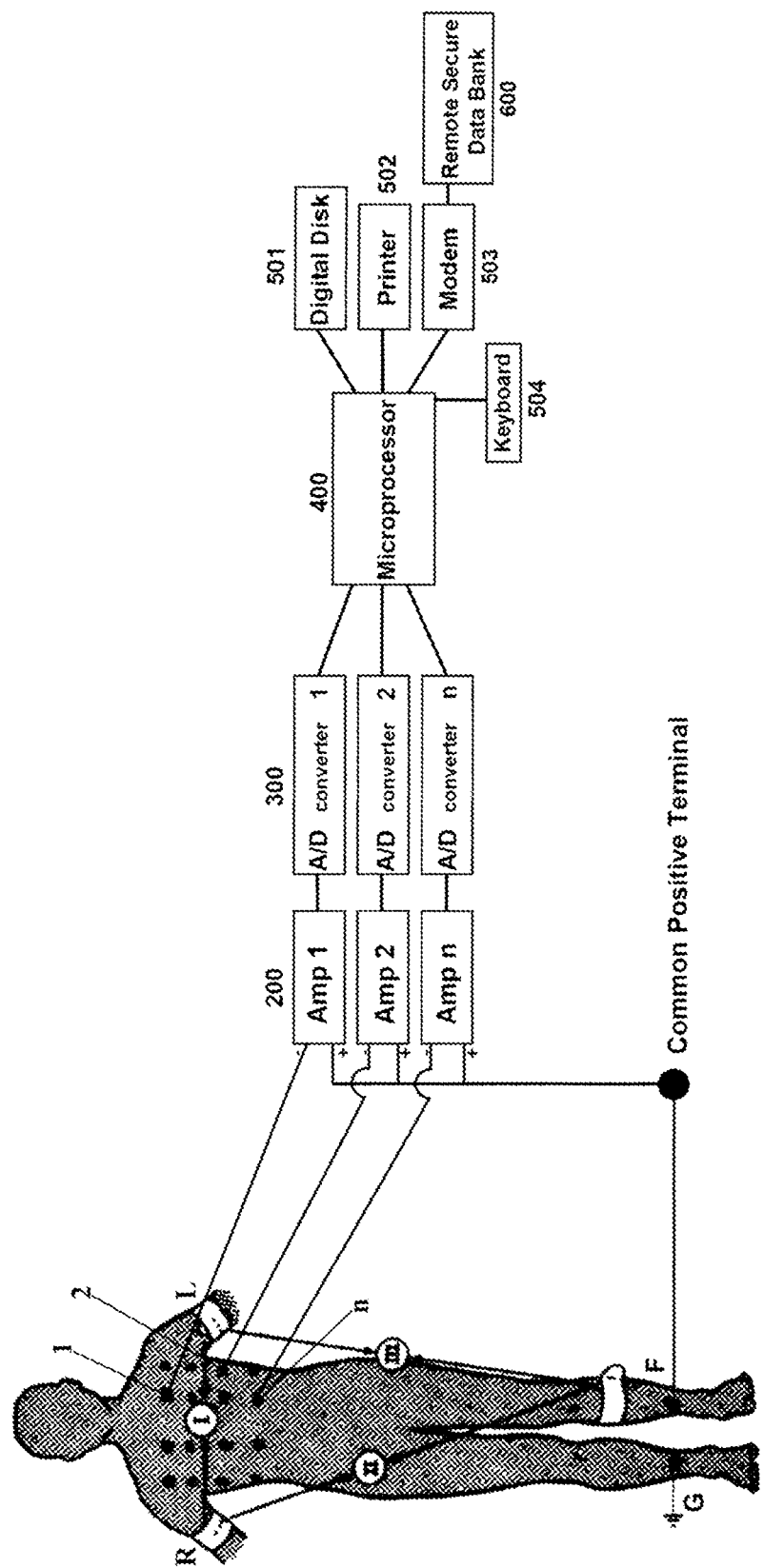
FIG. 1 is a block diagram of an electrocardiographic method in which the positive terminals of amplifiers 1 to n (n=15-100) are connected to a Common Positive terminal that is connected, through connecting means F, to an electrode placed on the left leg of the subject. The negative terminal of amplifiers 1 to n are connected, through connecting means 1 to n, to electrodes placed on the cephalic two thirds of the subject's torso.

To emphasize the difference between the present invention and the standard leads of today's electrocardiographic art, said leads are schematized in the figure of the subject.

DETAILED DESCRIPTION OF THE INVENTION

In view of the findings described above and the innumerable empirical decisions and theories in today's electrocardiography, and the need for a modified electrocardiograph that will unify the recording, interpretation and storing of all the electrocardiographic digital data obtained, the following modifications of the electrocardiograph and the new method was developed. A first step is to recognize that all of the recorded leads in today's art are bipolar. By standardizing one of the electrodes, the positive electrode, all the changes that are recorded are easier to understand. Today's practice of multiple Central electrodes, four in total, and different polarity and electrodes to obtain the three standard leads and nine unipolar leads do not allow a clear understanding of the potentials generated by each myocardial structure on very specific areas of the torso.

The number of Amplifiers varies from 15 for a portable electrocardiograph to a 100 for institutional or research use. The placement of the negative exploring electrodes differs from the traditional electrocardiograms. They are to be placed on the subject's cephalic two thirds of the torso on the areas were the Body Surface Maps show the prevalence of the minimal and maximal values for each wave and segments of the electrocardiographic trace. Each lead will be identified by the placement of the negative electrode by the use of easily recognizable anatomical reference points on the anterior and posterior surfaces of the body and by the distance to those points from the anterior or posterior midlines. On the anterior surface of the body, the points of reference are:
  a) The supra-sternal notch,
  b) The inter-costal spaces and
  c) The xiphoid.
On the posterior surface they are:
  a) The spinal process of the sixth cervical spine and
  b) The inter-vertebral spaces of T1 to T12-L1.

The measurements are to be done from the medial line along lines that intersect the reference points perpendicularly. The medial axilar line is the limit between anterior and posterior surfaces of the body. On the anterior surface two measurements should be included for electrodes placed above the sternal notch or below the xiphoid. They are: the distance from the reference point to the point where the medial line is transected by the perpendicular line that passes through the electrode, and the distance from said point in the mid-line to the electrode site to facilitate recording electrocardiograms identical to the original since placement is crucial in thoracic leads.

The embodiments according to the present invention will now be described in detail with reference to the drawings. The different electronic components described in the embodiments, amplifiers, A/D multiplexers, digital filters, calculators, analyzers, digital disks, modems, keyboards and printers that are part of today's electrocardiographs are commercially available components.

FIG. 1 shows a first embodiment of the present invention. As shown, the subject is positioned so that the cephalic two thirds of his torso, through the desired: number of electrodes n (n=15-100), is connected, through connectors 1 to n, to the negative terminal of high-gain, high frequency, low-noice differenctial electrocardiographic amplifiers 1 to n and the left leg is connected, through connecting means F, to the Common Positive Terminal of the electrocardiograph and from the . . . .

Common Positive Terminal to the positive terminals of high-gain, high frequency, low-noise differential electrocardiographic amplifiers 1 to n to generate a Bipolar, Non-Vectorial, Truncal Electrocardiographic Lead electrocardiogram. The figure shows a Ground Electrode on the right leg connected through connecting means G to the amplifiers' ground terminal to reduce noise. Each identical high-gain, high frequency, low-noise differential electrocardiographic amplifier 1 to n has an input isolation switch to prevent current leakage to the subject.

Each amplifier is connected to its own individual Analog-to-Digital Converter 300 (1, 2 to n). The A/D converter will sample the amplified analog electrocardiogram at a rate of 1,500 samples per second with 12-bit resolution to generate n digital data sets. The digital data sets are led to the Microprocessor (400).

Figure 2:
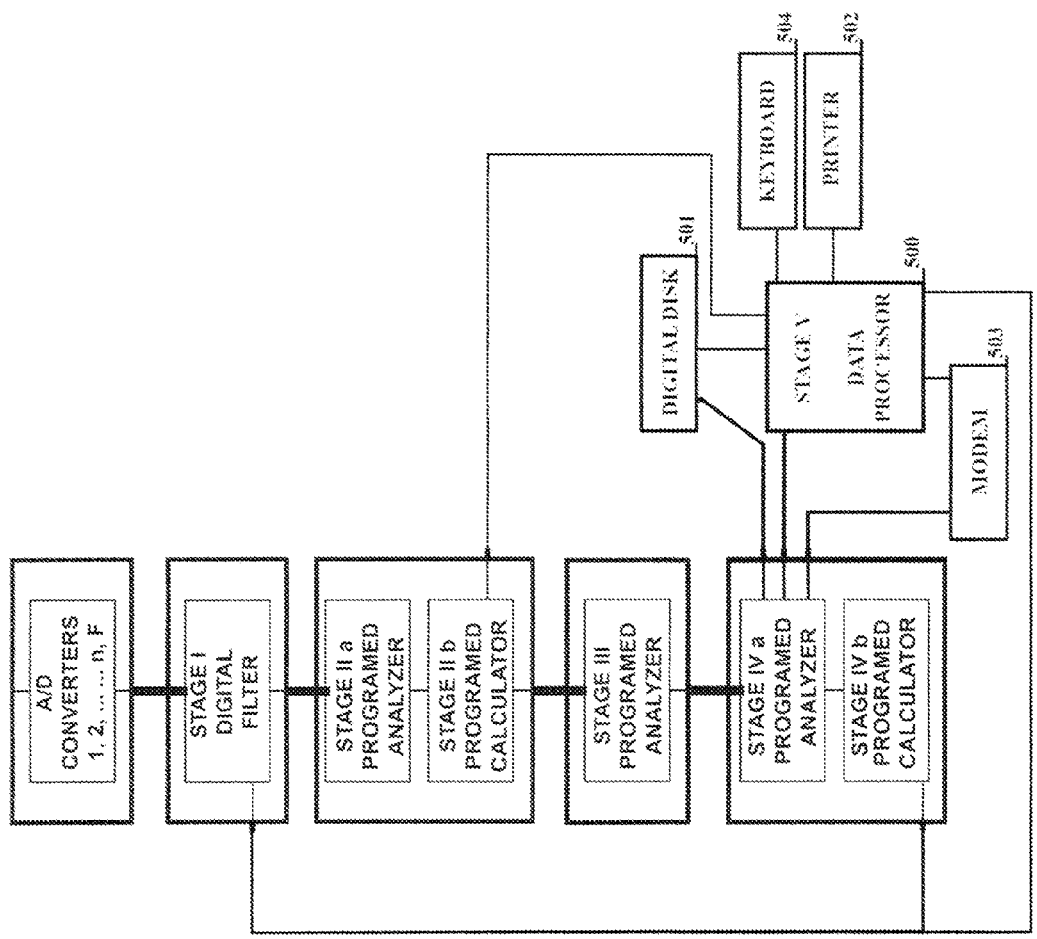
FIG. 2 is a master flow chart for the Microprocessor's different stages.

FIG. 2 shows the flow through the Microprocessor's different stages.
  1. A first stage is a Digital Filter with two-band pass filters between 0.5-55 Hz and 65-700 Hz and band stop filters between 55-65 Hz and all frequencies below 0.5 Hz and above 700 Hz. An n-filtered digital data sets are forwarded to a second, third and fourth stages of the microprocessor (400) connected to said digital filter.
  2. Said second stage, comprised of a Programmed Analyzer and calculator (402), pairs and identifies said n-filtered digital data sets obtained from the first stage. Pairing is done by selecting the minimal and the maximal values at predetermined instants of the electrocardiographic trace, wherein the predetermined instants are: a mid point between a start of a wave and a peak value of said wave; said peak value; a mid point between the peak value of the wave and an end of the wave of each P, Q, R, S, T, and U waves and at three instants: beginning, middle point and end, of each segment PQ, RST, TU, and TP. Identification is to be done by the electrocardiograph by: the number of the two selected amplifiers; the positive polarity is given to the maximal value and the negative polarity is given to the minimal value. The second stage substracts the minimal (negative) value from the maximal (positive) value of each pair of minimal and maximal values for each predetermined instant of the electrocardiographic trace to create a digital data set of differences. The digital data set of differences are fed to a third stage and to a data processor (500) connected to the second stage.
  3. In said third stage, the n filtered digital data sets from the first stage are compared to the digital data set of differences from the second stage to obtain approximate values generated by the electrode placed on the left leg of said subject. The approximate values generated by said electrode placed on the left leg and the digital data sets of differences are fed to a fourth stage connected to the third stage.

4. Said fourth stage, comprised of a programmed calculator and a data analyzer, adds said approximate values generated by the left leg to the n digital data sets from the first stage, the addition giving a good approximation of a value generated by each individual electrode 1 to n (n=15-100) on the cephalic two-thirds of the torso. All said approximate values generated by each electrode 1 to n; said approximate values of the electrode on the left leg and the digital data set of differences are fed to a Data Processor (500) connected to the fourth stage.

5. In said fifth stage, the data processor (500) stores information input by an operator through keyboard (504), wherein the information comprises, the identity of the subject including relevant personal and medical history data and the identify of each n amplifier by the anatomical placement of the electrode n connected to each said amplifier's negative terminal. Processor (500) then generates Identified Digital Data Sets comprising the approximate values generated by each electrode 1 to n; the approximate values of the electrode on the left leg, the digital data sets of differences; the personal and medical history of the patient; and the anatomical placement of each electrode 1 to n connected to amplifiers 1 to n.

6. If there are no previous identified digital data sets stored for the patient, the identified digital data sets are fed to: a printer (502) to print an electrocardiogram using the approximate values generated by each electrode 1 to n, a disk drive (501) and/or a modem (503) to save said identified digital data sets of said subject on a digital disk (501) or/and said modem (503) to be saved on a remote secure digital data bank (600).

7. If there are previous identified digital data sets stored for the patient, the stored identified digital data sets are retrieved from the digital disk and fed to the microprocessor's fourth stage analyzer to find if there are differences between present and prior identified digital data sets.

8. If no changes are found no new digital data sets are printed, stored to the digital disk, and/or saved on the remote secure data bank.

9. If there are changes, such changes will be reported in new digital data sets and fed to the Data Processor (500): to be printed (502); to be stored in a digital disk (501); and/or the modem (503) to be stored on a safe Digital data bank (600).

Figure 3:
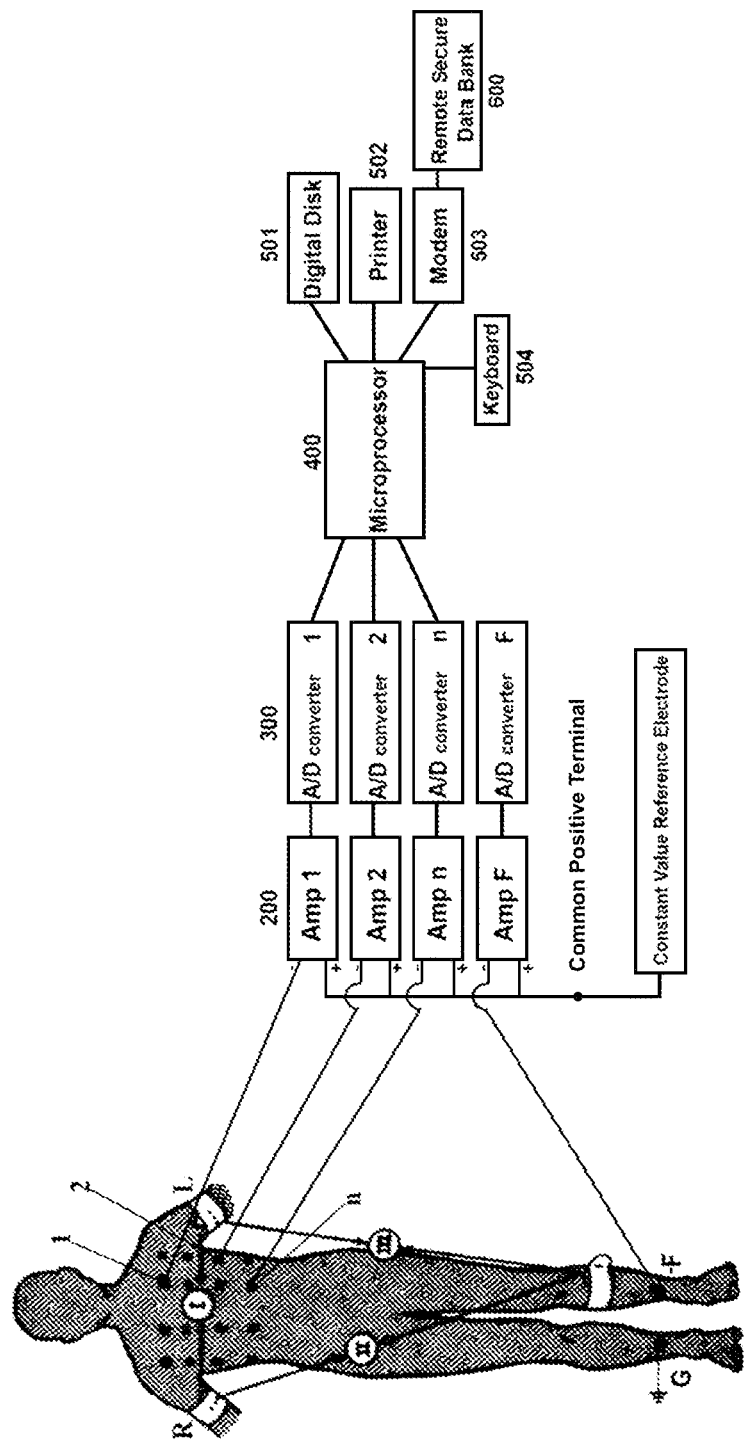
FIG. 3 is a block diagram of an Electrocardiographic method in which the positive terminals of amplifiers 1 to n and F are connected to a "Constant Value Electrode" and the negative terminals of amplifiers 1 to n are connected to electrodes placed on the cephalic two thirds of the subject's torso and the negative terminal of amplifier F is connected, through connecting means F, to an electrode placed on the subject's left leg.

FIG. 3 shows a second embodiment of the present invention. To generate "unipolar" electrocardiograms, a subject is positioned so that the cephalic two thirds of the torso are connected through connectors 1 to n (n=14-100) to n electrodes. The positive terminal of amplifiers 200 (1 to n) and amplifier F are connected to a "Constant Value Electrode". The negative terminal of amplifiers 200 (1 to n) are connected to connectors 1 to n and the negative terminal of amplifier F is connected to a left leg of a patient using connector-F.

1. The n electrodes are connected to the negative terminal of each individual high-gain, high frequency, low-noise, input-switch-insulated differential electrocardiographic amplifier 200 (1 to n). The positive terminals of amplifiers 200 (1 to n and F) are connected to a Constant Value Reference Electrode.

2. Amplified analog electrocardiograph signals obtained from amplifiers 200 (1 to n and F) are fed to individual analog/digital converters 300 (1 to n and F) The converters 300 (1 to n and F) will sample the 1 to n and F amplified analog electrocardiograph signals at a rate of 1,000 samples per second with 12-bit resolution to generate n and F digital data sets that are fed to a Microprocessor (400) connected to amplifiers 200 and A/D converters 300.

3. A first stage is a Digital Filter with two-band pass filters between 0.5-55 Hz and 65-1000 Hz and band stop filters between 55-65 Hz and all frequencies below 0.5 Hz and above 1000 Hz. N filtered digital data sets are forwarded to a fifth stage data processor (500) connected to said digital filter.

4. In said fifth stage the data processor (500)stores information input by an operator through keyboard (504), wherein the information comprises, the identity of said subject including relevant personal and medical history data and the identity of each n amplifier by an anatomical placement of said electrode n connected to each said amplifier's 200 (1 to n) negative terminal. Processor (500) then generates identified digital data sets comprising the n digital data set; the F digital data set; the personal and medical history of the patient; and the anatomical placement of each electrode 1 to n connected to amplifiers 200 (1 to n).

5. If there are no previous identified digital data sets stored for the patient, the identified digital data sets are: fed directly to a printer (502) to to print an electrocardiogram using the n digital data set, to a disk drive (501), and/or to a modem (503) to send the digital data sets to be stored in a secure remote digital data bank (600).

6. If the previous identified digital data set stored for the patient was bipolar, said n digital data sets and F digital data sets, are fed to the microprocessor's second stage programmed calculator to individually subtract digital data set F from the digital data set n to generate Bipolar, Non-Vectorial, Truncal Electrocardiographic Leads.

7. These Bipolar, Non-Vectorial Truncal Electrocardiographic Leads are fed into the second, third and fourth stages of the microprocessor and processed in these stages as described in the previous embodiment, wherein the Bipolar, Non-Vectorial Truncal Electrocardiographic Leads replace the n filtered digital data set.

8. If the previous identified digital data set stored for the patient was "unipolar", the n digital data set of the identified digital data sets retrieved from said disk driver (501) are fed to the microprocessor's fourth stage. Said stage's analyzer compares the previous n digital data set of unipolar data with the new n digital data set of unipolar data.

9. The subsequent stages follow the steps 8and 9 described in the previous embodiment.

Figure 4:
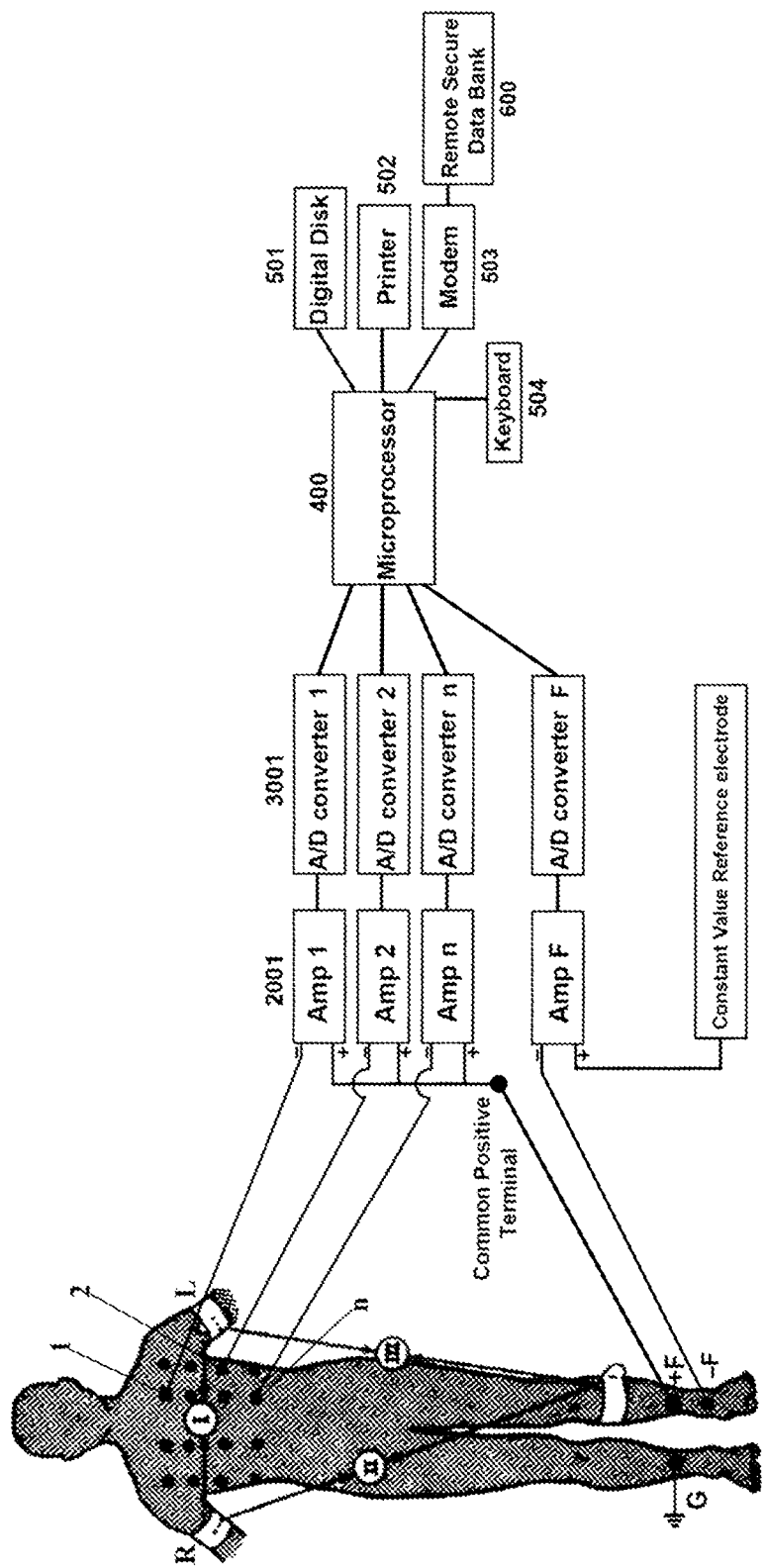
FIG. 4 is a block diagram of an Electrocardiographic method and apparatus in which the negative terminals of amplifiers 1 to n are connected, through connectors 1 to n, to the subject's torso and the positive terminals of amplifiers 1 to n are connected, through connector+F, to the subject's left leg. The negative terminal of amplifier F is connected, through connector−F, to the left leg and the positive terminal of amplifier F is connected to the constant value reference electrode.

FIG. 4, shows a third embodiment of the present invention. To generate Bipolar, Non-Vectorial, Truncal Electrocardiographic Leads a subject is positioned so that the cephalic two thirds of the torso are connected, through connectors, 1, 2, to n, to a respective negative terminal of each individual high-gain, high-frequency, low-noise, input-switch-insulated differential electrocardiographic amplifier 2001 (1, 2 to n). The positive terminal of amplifiers 2001 (1, 2 to n, (n=14-100)) are connected to a Common Positive Terminal and said common positive terminal is connected through, connector +F, to an extremity. The negative terminal of amplifier F is connected, through connector −F, to an electrode placed on said extremity and a positive terminal of amplifier F is connected to a "Constant Value Reference Electrode".
1. Step 1 is equal to the step of the first embodiment.
2. A second stage, comprised of a Programmed Analyzer and calculator, pairs and identifies said n filtered digital data sets obtained from the first stage. Pairing is done by selecting the minimal and the maximal values at predetermined instants of the electrocardiographic trace, wherein the predetermined instants are: a mid point between a start of a wave and a peak value of said wave; said peak value; a mid point between the peak value of the wave and an end of the wave of each P, Q, R, S, T, and U waves and at three instants: beginning, middle point and end, of each segment PQ, RST, TU, and TP. Identification is to be done by the electrocardiograph by: the number of the two selected amplifiers; the positive polarity is given to the maximal value and the negative polarity is given to the minimal value. The second stage subtracts the minimal (negative) value from the maximal (positive) value of each pair of minimal and maximal values for each predetermined instant of the electrocardiographic trace to create a digital data set of differences. The digital data sets obtained by amplifier F and said digital data set of differences are fed to a third stage and to a data processor (500) connected to the second stage.
3. In said third stage there are two options: (1) obtain the approximate values generated by the left leg, as is done in the first embodiment or (2) obtain the real unipolar values of all the recorded signals from the n electrodes. To calculate the real unipolar signals, the digital data set from amplifier F has to be added to the n filtered digital data sets and the digital data set of differences. The real unipolar signals are sent to said data processor (500) connected to the third stage.
4. The following stages are the same as in the previous embodiments, wherein the real unipolar signals replace the approximate values generated by the left leg if option (2) is selected from the third stage.

Advantages

Besides the abolition of the erroneous Hypothesis accepted by today's art electrocardiography, the new Bipolar, Non-Vectorial, Truncal Electrocardiogram will facilitate the diagnosis of the pathology of the myocardium by recording from areas closer to the auricles and ventricles of the myocardium with only one distal electrode as reference. The following diagnosis will be easier to identify:
1. Leads recorded from the right peri-clavicular areas will facilitate the recognition of:
    Arrhythmias of the auricles.
    Arrhythmias of supra-ventricular origin.
    Hypertrophy of the auricles.
    A-V blocks
2. Leads from the areas where electrical potential generated by the right ventricle are prevalent will facilitate the recognition of:
    Arrhythmias originating on the different structures of the Bundle of His, especially of the right branch.
    Arrhythmias of the right ventricle.
    Wolff-Parkinson-White Syndrome.
    Lown-Ganong-Levine Syndrome
    Right Bundle Branch Block
    Hypertrophy or enlargement of the right Ventricle.
    Ischemia of the right ventricle.
    Right ventricular hypertension.
    Right Ventricular Hypertrophy.
    Localization and extension of right ventricular infarcted area in the antero lateral surface.
3. Leads from the areas where electrical potentials generated by the contraction of the antero-lateral surface of the left ventricle are prevalent will facilitate the recognition of:
    Arrhythmias originating in the antero-lateral surface of the left ventricle.
    Ischemia of the antero-lateral surface of the left ventricle
    Infarct of the anterior descending coronary artery.
    Left Bundle Branch Block.
    Left Anterior Hemi-block.
    Aberrant Ventricular Depolarization.
    Hypertrophy of the left ventricle.
4. Leads from the areas where electrical potentials generated by the contraction of the postero-inferior surface of the left ventricle are prevalent will facilitate the recognition of:
    Arrhythmias generated in the postero-inferior surface of the left ventricle.
    Infarction of the inferior surface of the left ventricle.
    Infarcts or angina originating from occlusion of posterior coronary artery.
    Left Bundle Branch Block.
    Left Ventricular Aneurism.
5. Leads from the areas were the posterior surface of the left ventricle are prevalent will facilitate the recognition of:
    Arrhythmias originating from the posterior surface of the left Ventricle.
    Infarcts of the posterior wall of the left ventricle.
    Left Bundle Branch Block.
    Left Posterior Hemi-block.
    Left ventricular hypertrophy.
    Angina due to stenosis of the posterior coronary artery.

Since certain changes may be made in the above constructions without departing from the scope of the invention, it is intended that all matter contained in the above description be interpreted as illustrative and not limiting in any way. It is also to be understood that the following claims are to cover all generic and specific features of the invention described herein, and all statements of the scope of the invention which, as a matter of language, might be said to fall there between.

Definition List

| Term | Definition |
| --- | --- |
| "Unipolar" | Measurements between terminal pairs when one terminal is connected to a "Constant Value Electrode" an the other is connected to an electrode placed on the subject. |
| "Bipolar" | Measurements between terminal pairs when both terminals are connected to electrodes placed on the subject. |
| "Ground Electrode" | Electrical connection to the ground. |
| "Constant Value Electrode" | Electrode connected to an element of known electrical potential that is constant and free of interference from the electrical fields of the subject and the environment. |
| "Value" | Electrical potential difference between amplifier terminal pairs. |
| "Exploring Negative Terminals" | Negative terminal of the individual amplifiers. |
| "Common Positive Terminals" | Positive terminal of the individual amplifiers. |
| "Exploring Negative Electrodes | Electrodes connected to the negative terminal of the amplifiers and placed on the subject's torso. |
| "Common Positive Electrode" | Electrode connected to the positive terminal of the amplifiers and placed on the distal third of either leg or right arm. |

-continued

| Term | Definition |
| --- | --- |
| "Electrocardiographic Lead" | Difference between the electrical pairs of each individual amplifier and identified by the anatomical site of the "Exploring Negative Electrode" in the subject's torso. |
| "Digital disk" | Systems used to store digital data, Floppy disk, CD, Hard disk, DVD, etc. |

The invention claimed is:

1. A modified electrocardiograph configured to record electrical activity of specific myocardial structures of a patient, the electrocardiograph comprising:
- a Common Positive Electrode that is adapted to be placed on an extremity of a patient, wherein the Common Positive Electrode is connected to a Common Positive Terminal;
- a plurality of amplifiers (1, 2, to n), n=15-100, wherein a positive terminal of each of the plurality of amplifiers is connected to the Common Positive Terminal and wherein a negative terminal of each of the plurality of amplifiers is connected to a corresponding Exploring Negative Electrode (1, 2, to n) that is adapted to be placed on a torso of the patient;
- a plurality of A/D converters (1, 2, to n), n=15-100, each connected to a respective one of said plurality of amplifiers, wherein said plurality of A/D convertors are connected to a microprocessor of the modified electrocardiograph, said microprocessor comprising:
- a first stage configured to receive signals from each of said Exploring Negative Electrodes and said Common Positive Electrode and is further configured to filter the received signals, thereby creating n-filtered digital data sets;
- a second stage comprising a programmed analyzer configured to select and pair minimum and maximal values of the n-filtered digital data sets at specific instants of an electrocardiographic trace and a calculator configured to subtract the minimum value from the maximal value of each pair of minimum and maximal values for each specific instant of the electrocardiographic trace to create a digital data set of differences;
- a third stage comprising a programmed analyzer configured to compare the n-filtered digital data sets from the first stage with the digital data set of differences from the second stage to create a digital data set of approximate values; and
- a fourth stage comprising a programmed calculator and data analyzer configured to add the digital data set of approximate values generated by the third stage to the n-filtered digital data sets from the first stage.

2. A modified electrocardiograph configured to record electrical activity of specific myocardial structures of a patient, the electrocardiograph comprising:
- a Constant Value Reference Electrode connected to a Common Positive Terminal;
- a plurality of amplifiers (1, 2, to n), n=15-100, wherein a positive terminal of each of the plurality of amplifiers is connected to the Common Positive Terminal and wherein a negative terminal of each of the plurality of amplifiers is connected to a corresponding Exploring Negative Electrode (1, 2, to n) that is adapted to be placed on a torso of the patient;
- an amplifier F, wherein a positive terminal of amplifier F is electrically connected to said Constant Value Reference Electrode; and a negative terminal of amplifier F is connected to a negative Exploring Electrode that is adapted to be placed on an extremity of a patient;
- a plurality of A/D converters (1, 2, to n), n=15-100, each connected to a respective one of said plurality of amplifiers and an A/D converter F connected to amplifier F, wherein said plurality of A/D convertors and A/D converter F are connected to a microprocessor of the modified electrocardiograph, said microprocessor comprising:
- a first stage configured to receive and filter signals from each of said Exploring Negative Electrodes adapted to be placed on a torso of the patient and said Constant Value Reference Electrode obtained with the plurality of amplifiers (1, 2, to n), n=15-100 to create n-filtered digital data sets and is further configured to receive and filter signals from the Exploring Negative Electrode adapted to be placed on an extremity of the patient and said Constant Value Reference Electrode obtained with amplifier F to create an F filtered digital data set;
- a second stage comprising a programmed analyzer configured to subtract the F digital data set from the n-filtered digital data sets to create a digital data set of bipolar values; to select and pair minimum and maximal values of the digital data set of bipolar values at specific instants of an electrocardiographic trace and a calculator configured to subtract the minimum value from the maximal value of each pair of minimum and maximal values for each specific instant of the electrocardiographic trace to create a digital data set of differences;
- a third stage comprising a programmed analyzer configured to compare the digital data set of bipolar values from the second stage with the digital data set of differences from the second stage to create a digital data set of approximate values; and
- a fourth stage comprising a programmed calculator and data analyzer configured to add the digital data set of approximate values generated by the third stage to the digital data set of bipolar values from the second stage.

3. A modified electrocardiograph configured to record electrical activity of specific myocardial structures of a patient, the electrocardiograph comprising:
- a Common Positive Electrode that is adapted to be placed on an extremity of a patient, wherein the Common Positive Electrode is connected to a Common Positive Terminal;
- a plurality of amplifiers (1, 2, to n), n=15-100, wherein a positive terminal of each of the plurality of amplifiers is connected to the Common Positive Terminal and wherein a negative terminal of each of the plurality of amplifiers is connected to a corresponding Exploring Negative Electrode (1, 2, to n) that is adapted to be placed on a torso of the patient;
- an amplifier F, wherein a positive terminal of amplifier F is electrically connected to a Constant Value Reference Electrode; and a negative terminal of amplifier F is electrically connected to a negative exploring electrode adapted to be placed on an extremity of a patient
- a plurality of A/D converters (1, 2, to n), n=15-100, each connected to a respective one of said plurality of amplifiers, and an A/D converter F connected to amplifier F, wherein said plurality of A/D convertors and A/D converter F are connected to a microprocessor of the modified electrocardiograph, said microprocessor comprising:
- a first stage configured to receive and filter signals from each of said Exploring Negative Electrodes adapted to be placed on a torso of the patient and said Common Positive Electrode obtained with the plurality of amplifiers (1, 2, to n), n=15-100 to create n-filtered digital data sets and is further configured to receive and filter signals from the Exploring Negative Electrode adapted to be placed on an extremity of the patient and said Constant Value Reference Electrode obtained with amplifier F to create an F filtered digital data set;

a second stage comprising a programmed analyzer configured to select and pair minimum and maximal values of the n-filtered digital data sets at specific instants of an electrocardiographic trace and a calculator configured to subtract the minimum value from the maximal value of each pair of minimum and maximal values for each specific instant of the electrocardiographic trace to create a digital data set of differences;

a third stage comprising a programmed analyzer configured to compare the n-filtered digital data sets from the first stage with the digital data set of differences from the second stage to create a digital data set of approximate values; and further configured to add the F digital data set to both the n-filtered digital data sets and the digital data set of differences to create a digital data set of unipolar values a fourth stage comprising a programmed calculator and data analyzer configured to add the digital data set of approximate values generated by the third stage to the n-filtered digital data sets from the first stage; and further configured to add the digital data set of unipolar values generated by the third stage to the n-filtered digital data sets from the first stage.

* * * * *